US012697396B2

(12) United States Patent
Riemer et al.

(10) Patent No.: US 12,697,396 B2
(45) Date of Patent: *Aug. 4, 2026

(54) REUSABLE BATTERY INDICATOR WITH ELECTRICAL LOCK AND KEY

(71) Applicant: DURACELL U.S. OPERATIONS, INC., Wilmington, DE (US)

(72) Inventors: Joern Riemer, Santa Clara, CA (US); Robert Pavlinsky, Oxford, CT (US); Jordan Bourilkov, Bethany, CT (US); Steven J. Specht, Brookfield, CT (US); George Turco, Wilmington, DE (US); Sergio Coronado, Bethel, CT (US)

(73) Assignee: DURACELL U.S. OPERATIONS, INC., Wilmington, DE (US)

( * ) Notice: Subject to any disclaimer, the term of this patent is extended or adjusted under 35 U.S.C. 154(b) by 165 days.

This patent is subject to a terminal disclaimer.

(21) Appl. No.: 18/219,841

(22) Filed: Jul. 10, 2023

(65) Prior Publication Data

US 2024/0000910 A1 Jan. 4, 2024

Related U.S. Application Data

(60) Continuation of application No. 17/224,000, filed on Apr. 6, 2021, now Pat. No. 11,696,942, which is a
(Continued)

(51) Int. Cl.
*H01M 10/48* (2006.01)
*A61K 39/00* (2006.01)
(Continued)

(52) U.S. Cl.
CPC .......... *A61K 48/00* (2013.01); *A61K 39/0011* (2013.01); *A61P 35/00* (2018.01);
(Continued)

(58) Field of Classification Search
CPC ...... H01R 13/639; H01R 13/62; H01R 13/00; H01R 13/6683; G01R 31/36;
(Continued)

(56) References Cited

U.S. PATENT DOCUMENTS

| | | | |
|---|---|---|---|
| 3,354,565 A | 11/1967 | Emmons et al. | |
| 3,992,228 A | 11/1976 | Depoix | |

(Continued)

FOREIGN PATENT DOCUMENTS

| | | |
|---|---|---|
| CN | 1084281 A | 3/1994 |
| CN | 1163020 A | 10/1997 |

(Continued)

OTHER PUBLICATIONS

Chinese Patent Application No. 201780068033.1, Office Action, dated Jan. 12, 2022.
(Continued)

*Primary Examiner* — Benyam Haile
(74) *Attorney, Agent, or Firm* — MARSHALL, GERSTEIN & BORUN LLP

(57) ABSTRACT

A reusable battery indicator includes a voltage sensor, a communication circuit communicatively connected to the voltage sensor, an antenna operatively coupled to the communication circuit, and a connector. The connector is electrically connected to the voltage sensor, and the connector is adapted to be removably connected to a battery, thereby providing an electrical connection between the voltage sensor and the battery. An electrical circuit is completed between the voltage sensor and the battery and the voltage sensor. The connection mechanism includes part of an electrical lock and key assembly.

20 Claims, 6 Drawing Sheets

Related U.S. Application Data continuation of application No. 16/215,383, filed on Dec. 10, 2018, now Pat. No. 10,971,769, which is a division of application No. 15/340,789, filed on Nov. 1, 2016, now Pat. No. 10,151,802.

(51) Int. Cl.

| | |
|---|---|
| *A61K 48/00* | (2006.01) |
| *A61P 35/00* | (2006.01) |
| *C12N 15/86* | (2006.01) |
| *G01R 31/364* | (2019.01) |
| *G01R 31/371* | (2019.01) |
| *G01R 31/382* | (2019.01) |
| *G01R 31/3842* | (2019.01) |
| *G01R 31/389* | (2019.01) |
| *G01R 31/392* | (2019.01) |
| *H01M 6/50* | (2006.01) |
| *H01M 10/42* | (2006.01) |
| *H01R 13/639* | (2006.01) |
| *H01R 13/66* | (2006.01) |
| *C12Q 1/6886* | (2018.01) |
| *G01K 1/024* | (2021.01) |
| *G01N 33/575* | (2026.01) |
| *G01R 31/36* | (2020.01) |
| *H01M 50/103* | (2021.01) |
| *H01M 50/107* | (2021.01) |

(52) U.S. Cl.
CPC ........... *C12N 15/86* (2013.01); *G01R 31/364* (2019.01); *G01R 31/371* (2019.01); *G01R 31/382* (2019.01); *G01R 31/3842* (2019.01); *G01R 31/389* (2019.01); *G01R 31/392* (2019.01); *H01M 6/505* (2013.01); *H01M 10/425* (2013.01); *H01M 10/4285* (2013.01); *H01M 10/48* (2013.01); *H01M 10/488* (2013.01); *H01R 13/639* (2013.01); *H01R 13/6683* (2013.01); *C12Q 1/6886* (2013.01); *G01K 1/024* (2013.01); *G01N 33/575* (2026.01); *G01R 31/36* (2013.01); *H01M 10/4257* (2013.01); *H01M 2010/4278* (2013.01); *H01M 10/482* (2013.01); *H01M 50/103* (2021.01); *H01M 50/107* (2021.01)

(58) Field of Classification Search
CPC .............. G01R 31/364; G01R 31/3644; G01R 31/3646; G01R 31/371; G01R 31/38; G01R 31/378; H01M 10/488; H01M 10/48

See application file for complete search history.

(56) References Cited

U.S. PATENT DOCUMENTS

| | | | |
|---|---|---|---|
| 3,993,985 | A | 11/1976 | Chopard et al. |
| 4,117,475 | A | 9/1978 | Ebihara et al. |
| 4,149,146 | A | 4/1979 | Ebihara et al. |
| 4,238,554 | A | 12/1980 | Barrella |
| 4,302,751 | A | 11/1981 | Nakauchi et al. |
| 4,460,870 | A | 7/1984 | Finger |
| 4,482,615 | A | 11/1984 | Rosansky et al. |
| 4,598,243 | A | 7/1986 | Kawakami |
| 4,654,280 | A | 3/1987 | Bailey |
| 4,723,656 | A | 2/1988 | Kiernan et al. |
| 4,759,765 | A | 7/1988 | Van Kampen |
| 4,808,497 | A | 2/1989 | Blomgren et al. |
| 4,860,185 | A | 8/1989 | Brewer et al. |
| 4,952,330 | A | 8/1990 | Leger et al. |
| 5,015,544 | A | 5/1991 | Burroughs et al. |
| 5,032,825 | A | 7/1991 | Kuznicki |
| 5,188,231 | A | 2/1993 | Kivell et al. |
| 5,200,686 | A | 4/1993 | Lee |
| 5,219,683 | A | 6/1993 | Webber |
| 5,231,356 | A | 7/1993 | Parker |
| 5,250,905 | A | 10/1993 | Kuo et al. |
| 5,290,414 | A | 3/1994 | Marple |
| 5,339,024 | A | 8/1994 | Kuo et al. |
| 5,355,089 | A | 10/1994 | Treger |
| 5,366,832 | A | 11/1994 | Hayashi et al. |
| 5,389,458 | A | 2/1995 | Weiss et al. |
| 5,389,470 | A | 2/1995 | Parker et al. |
| 5,396,177 | A | 3/1995 | Kuo et al. |
| 5,418,085 | A | 5/1995 | Huhndorff et al. |
| 5,418,086 | A | 5/1995 | Bailey |
| 5,424,722 | A | 6/1995 | Inada et al. |
| 5,438,607 | A | 8/1995 | Przygoda, Jr. et al. |
| 5,449,570 | A | 9/1995 | Inkmann et al. |
| 5,458,992 | A | 10/1995 | Bailey |
| 5,458,997 | A | 10/1995 | Crespi et al. |
| 5,491,038 | A | 2/1996 | DePalma et al. |
| 5,494,496 | A | 2/1996 | Huhndorff et al. |
| 5,514,491 | A | 5/1996 | Webber |
| 5,525,439 | A | 6/1996 | Huhndorff et al. |
| 5,543,246 | A | 8/1996 | Treger |
| 5,569,556 | A | 10/1996 | Bohmer |
| 5,587,573 | A | 12/1996 | Owen et al. |
| 5,596,278 | A | 1/1997 | Lin |
| 5,607,790 | A | 3/1997 | Hughen et al. |
| 5,627,472 | A | 5/1997 | Ofer et al. |
| 5,633,592 | A | 5/1997 | Lang |
| 5,640,150 | A | 6/1997 | Atwater |
| 5,654,640 | A | 8/1997 | Bailey |
| 5,691,083 | A | 11/1997 | Bolster |
| 5,737,114 | A | 4/1998 | Bailey |
| 5,786,106 | A | 7/1998 | Armani |
| 5,798,933 | A | 8/1998 | Nicolai |
| 5,849,046 | A | 12/1998 | Bailey |
| 5,925,479 | A | 7/1999 | Wei et al. |
| 5,959,568 | A | 9/1999 | Woolley |
| 5,963,012 | A | 10/1999 | Garcia et al. |
| 6,014,014 | A | 1/2000 | Owen et al. |
| 6,084,523 | A | 7/2000 | Gelnovatch et al. |
| 6,127,062 | A | 10/2000 | Sargeant et al. |
| 6,143,439 | A | 11/2000 | Yoppolo et al. |
| 6,156,450 | A | 12/2000 | Bailey |
| 6,169,397 | B1 | 1/2001 | Steinbach et al. |
| 6,171,729 | B1 | 1/2001 | Gan et al. |
| 6,208,235 | B1 | 3/2001 | Trontelj |
| 6,218,054 | B1 | 4/2001 | Webber |
| 6,252,377 | B1 | 6/2001 | Shibutani et al. |
| 6,275,161 | B1 | 8/2001 | Wan et al. |
| 6,300,004 | B1 | 10/2001 | Tucholski |
| 6,407,534 | B1 | 6/2002 | Mukainakano |
| 6,469,471 | B1 | 10/2002 | Anbuky et al. |
| 6,483,275 | B1 | 11/2002 | Nebrigic et al. |
| 6,587,250 | B2 | 7/2003 | Armgarth et al. |
| 6,617,069 | B1 | 9/2003 | Hopper et al. |
| 6,617,072 | B2 | 9/2003 | Venkatesan et al. |
| 6,627,353 | B1 | 9/2003 | Munshi |
| 6,670,073 | B2 | 12/2003 | Tucholski et al. |
| RE38,518 | E | 5/2004 | Tucholski |
| 6,730,136 | B2 | 5/2004 | Webber |
| 6,774,685 | B2 | 8/2004 | O'Toole et al. |
| 6,775,562 | B1 | 8/2004 | Owens et al. |
| 6,849,360 | B2 | 2/2005 | Marple |
| 6,979,502 | B1 * | 12/2005 | Gartstein ........... H01M 6/5044 429/7 |
| 6,990,171 | B2 | 1/2006 | Toth et al. |
| 7,067,882 | B2 | 6/2006 | Singh |
| 7,079,079 | B2 | 7/2006 | Jo et al. |
| 7,157,185 | B2 | 1/2007 | Marple |
| 7,386,404 | B2 | 6/2008 | Cargonja et al. |
| 7,474,230 | B2 | 1/2009 | Blom et al. |
| 7,489,431 | B2 | 2/2009 | Malmstrom et al. |
| 7,511,454 | B1 | 3/2009 | Legg |
| 7,561,050 | B2 | 7/2009 | Bhogal et al. |
| 7,576,517 | B1 | 8/2009 | Cotton et al. |
| 7,586,416 | B2 | 9/2009 | Ariyoshi et al. |
| 7,598,880 | B2 | 10/2009 | Powell et al. |

(56) References Cited

U.S. PATENT DOCUMENTS

| | | | |
|---|---|---|---|
| 7,606,530 | B1 | 10/2009 | Anderson et al. |
| 7,715,884 | B2 | 5/2010 | Book et al. |
| 7,741,970 | B2 | 6/2010 | Cunningham et al. |
| 7,745,046 | B2 | 6/2010 | Kim et al. |
| 7,768,236 | B2 | 8/2010 | Takamura et al. |
| 7,772,850 | B2 | 8/2010 | Bertness |
| 7,805,263 | B2 | 9/2010 | Mack |
| 7,911,182 | B2 | 3/2011 | Cargonja et al. |
| 7,944,368 | B2 | 5/2011 | Carter et al. |
| 8,031,054 | B2 | 10/2011 | Tuttle |
| 8,106,845 | B2 | 1/2012 | Savry |
| 8,119,286 | B2 | 2/2012 | Issaev et al. |
| 8,131,486 | B2 | 3/2012 | Leonard et al. |
| 8,344,685 | B2 | 1/2013 | Bertness et al. |
| 8,368,356 | B2 | 2/2013 | Nakashima et al. |
| 8,374,507 | B2 | 2/2013 | Hudson et al. |
| 8,424,092 | B2 | 4/2013 | Ikeuchi et al. |
| 8,427,109 | B2 | 4/2013 | Melichar |
| 8,471,888 | B2 | 6/2013 | George et al. |
| 8,478,552 | B2 | 7/2013 | Morita et al. |
| 8,652,670 | B2 | 2/2014 | Uchida |
| 8,653,926 | B2 | 2/2014 | Detcheverry et al. |
| 8,900,731 | B2 | 12/2014 | Bohne |
| 8,905,317 | B1 | 12/2014 | Hsu et al. |
| 9,037,426 | B2 | 5/2015 | Schaefer |
| 9,060,213 | B2 | 6/2015 | Jones |
| 9,076,092 | B2 | 7/2015 | Ritamaki et al. |
| 9,083,063 | B2 | 7/2015 | Specht et al. |
| 9,146,595 | B2 | 9/2015 | Forutanpour et al. |
| 9,167,317 | B2 | 10/2015 | DeMar |
| 9,189,667 | B2 | 11/2015 | Bourilkov et al. |
| 9,235,044 | B2 * | 1/2016 | Specht ..................... H02J 7/82 |
| 9,297,859 | B2 | 3/2016 | Mukaitani et al. |
| 9,312,575 | B2 | 4/2016 | Stukenberg et al. |
| 9,331,378 | B2 | 5/2016 | Merlin et al. |
| 9,415,499 | B2 * | 8/2016 | Brotto ................ H01M 50/296 |
| 9,425,487 | B2 | 8/2016 | Bertness |
| 9,453,885 | B2 | 9/2016 | Mukaitani et al. |
| 9,459,323 | B2 | 10/2016 | Mukaitani et al. |
| 9,461,339 | B2 | 10/2016 | Roohparvar |
| 9,478,850 | B2 | 10/2016 | Bourilkov et al. |
| 9,515,303 | B2 | 12/2016 | Lee et al. |
| 9,551,758 | B2 | 1/2017 | Bourilkov et al. |
| 9,568,556 | B2 | 2/2017 | Bourilkov et al. |
| 9,619,612 | B2 | 4/2017 | Kallfelz et al. |
| 9,639,724 | B2 | 5/2017 | Bourilkov et al. |
| 9,661,576 | B2 | 5/2017 | Tomisawa |
| 9,699,818 | B2 | 7/2017 | Grothaus et al. |
| 9,726,763 | B2 | 8/2017 | Dempsey et al. |
| 9,739,837 | B2 | 8/2017 | Bourilkov et al. |
| 9,746,524 | B2 | 8/2017 | Petrucelli |
| 9,774,210 | B1 | 9/2017 | Wright |
| 9,823,310 | B2 | 11/2017 | Bourilkov et al. |
| 9,841,462 | B2 | 12/2017 | Kim et al. |
| 9,843,220 | B2 | 12/2017 | Herrmann et al. |
| 9,869,726 | B2 | 1/2018 | Zumstein et al. |
| 9,882,250 | B2 | 1/2018 | Chappelle et al. |
| 9,887,463 | B2 | 2/2018 | Bourilkov et al. |
| 9,893,390 | B2 | 2/2018 | Specht et al. |
| 9,983,312 | B2 | 5/2018 | Dempsey et al. |
| 10,094,886 | B2 | 10/2018 | Bourilkov et al. |
| 10,151,802 | B2 | 12/2018 | Riemer et al. |
| 10,184,988 | B2 | 1/2019 | Bourilkov et al. |
| 10,297,875 | B2 | 5/2019 | Riemer et al. |
| 10,416,309 | B2 | 9/2019 | Dempsey et al. |
| 10,483,634 | B2 | 11/2019 | Bourilkov et al. |
| 2001/0005123 | A1 | 6/2001 | Jones et al. |
| 2001/0026226 | A1 | 10/2001 | Andersson et al. |
| 2002/0001745 | A1 | 1/2002 | Gartstein et al. |
| 2002/0086718 | A1 | 7/2002 | Bigwood et al. |
| 2002/0193955 | A1 | 12/2002 | Bertness et al. |
| 2003/0070283 | A1 | 4/2003 | Webber |
| 2003/0124417 | A1 | 7/2003 | Bertness et al. |
| 2003/0169047 | A1 | 9/2003 | Chen |
| 2003/0170537 | A1 | 9/2003 | Randell |
| 2003/0184493 | A1 | 10/2003 | Robinet et al. |
| 2003/0228518 | A1 | 12/2003 | Marple |
| 2004/0029007 | A1 | 2/2004 | Kusumoto et al. |
| 2004/0048512 | A1 | 3/2004 | Chen |
| 2004/0183742 | A1 | 9/2004 | Goff et al. |
| 2004/0189256 | A1 | 9/2004 | Sink |
| 2005/0038614 | A1 | 2/2005 | Botts et al. |
| 2005/0073282 | A1 | 4/2005 | Carrier et al. |
| 2005/0095508 | A1 | 5/2005 | Yamamoto |
| 2005/0112462 | A1 | 5/2005 | Marple |
| 2005/0162129 | A1 | 7/2005 | Mutabdzija et al. |
| 2005/0233214 | A1 | 10/2005 | Marple et al. |
| 2005/0258797 | A1 | 11/2005 | Hung |
| 2005/0277023 | A1 | 12/2005 | Marple et al. |
| 2006/0017581 | A1 | 1/2006 | Schwendinger et al. |
| 2006/0028179 | A1 | 2/2006 | Yudahira et al. |
| 2006/0043933 | A1 | 3/2006 | Latinis |
| 2006/0046152 | A1 | 3/2006 | Webber |
| 2006/0046153 | A1 | 3/2006 | Webber |
| 2006/0046154 | A1 | 3/2006 | Webber et al. |
| 2006/0047576 | A1 | 3/2006 | Aaltonen et al. |
| 2006/0163692 | A1 | 7/2006 | Detcheverry et al. |
| 2006/0168802 | A1 | 8/2006 | Tuttle |
| 2006/0170397 | A1 | 8/2006 | Srinivasan et al. |
| 2006/0208898 | A1 | 9/2006 | Swanson et al. |
| 2006/0247156 | A1 | 11/2006 | Vanderby et al. |
| 2006/0261960 | A1 | 11/2006 | Haraguchi et al. |
| 2007/0080804 | A1 | 4/2007 | Hirahara et al. |
| 2007/0096697 | A1 | 5/2007 | Maireanu |
| 2007/0108946 | A1 | 5/2007 | Yamauchi et al. |
| 2007/0182576 | A1 | 8/2007 | Proska et al. |
| 2007/0210924 | A1 | 9/2007 | Arnold et al. |
| 2007/0273329 | A1 | 11/2007 | Kobuse et al. |
| 2008/0053716 | A1 | 3/2008 | Scheucher |
| 2008/0076029 | A1 | 3/2008 | Bowden et al. |
| 2008/0079391 | A1 | 4/2008 | Schroeck et al. |
| 2008/0157924 | A1 | 7/2008 | Batra |
| 2008/0160392 | A1 | 7/2008 | Toya et al. |
| 2008/0206627 | A1 | 8/2008 | Wright |
| 2008/0218351 | A1 | 9/2008 | Corrado et al. |
| 2008/0252462 | A1 | 10/2008 | Sakama |
| 2009/0008031 | A1 | 1/2009 | Gould et al. |
| 2009/0009177 | A1 | 1/2009 | Kim et al. |
| 2009/0024309 | A1 | 1/2009 | Crucs |
| 2009/0041228 | A1 | 2/2009 | Owens et al. |
| 2009/0098462 | A1 | 4/2009 | Fujiwara et al. |
| 2009/0148756 | A1 | 6/2009 | Specht et al. |
| 2009/0155673 | A1 | 6/2009 | Northcott |
| 2009/0179763 | A1 | 7/2009 | Sheng |
| 2009/0214950 | A1 | 8/2009 | Bowden et al. |
| 2009/0263727 | A1 | 10/2009 | Josephs et al. |
| 2009/0273473 | A1 | 11/2009 | Tuttle |
| 2009/0289825 | A1 | 11/2009 | Trinkle |
| 2009/0297949 | A1 | 12/2009 | Berkowitz et al. |
| 2009/0308936 | A1 | 12/2009 | Nitzan et al. |
| 2009/0309545 | A1 | 12/2009 | Kunimitsu |
| 2010/0019733 | A1 | 1/2010 | Rubio |
| 2010/0030592 | A1 | 2/2010 | Evans et al. |
| 2010/0073003 | A1 | 3/2010 | Sakurai et al. |
| 2010/0081049 | A1 | 4/2010 | Holl et al. |
| 2010/0085008 | A1 | 4/2010 | Suzuki et al. |
| 2010/0087241 | A1 | 4/2010 | Nguyen et al. |
| 2010/0143753 | A1 | 6/2010 | Kim et al. |
| 2010/0209744 | A1 | 8/2010 | Kim |
| 2010/0219252 | A1 | 9/2010 | Kikuchi et al. |
| 2010/0295943 | A1 | 11/2010 | Cha et al. |
| 2010/0308974 | A1 | 12/2010 | Rowland et al. |
| 2011/0018777 | A1 | 1/2011 | Brown |
| 2011/0023130 | A1 | 1/2011 | Gudgel et al. |
| 2011/0104520 | A1 | 5/2011 | Ahn |
| 2011/0123874 | A1 | 5/2011 | Issaev et al. |
| 2011/0163752 | A1 | 7/2011 | Janousek et al. |
| 2011/0293969 | A1 | 12/2011 | Hoofman et al. |
| 2012/0021266 | A1 | 1/2012 | Marple et al. |
| 2012/0056002 | A1 | 3/2012 | Ritamaki et al. |
| 2012/0081774 | A1 | 4/2012 | De Paiva Martins et al. |
| 2012/0086615 | A1 | 4/2012 | Norair |
| 2012/0121943 | A1 | 5/2012 | Roohparvar |
| 2012/0183862 | A1 | 7/2012 | Gupta et al. |

(56) References Cited

U.S. PATENT DOCUMENTS

| | | |
|---|---|---|
| 2012/0190305 A1 | 7/2012 | Wuidart |
| 2012/0206102 A1 | 8/2012 | Okamura et al. |
| 2012/0206302 A1 | 8/2012 | Ramachandran et al. |
| 2012/0217971 A1 | 8/2012 | Deluca |
| 2012/0235870 A1 | 9/2012 | Forster |
| 2012/0277832 A1 | 11/2012 | Hussain |
| 2012/0299597 A1 | 11/2012 | Shigemizu |
| 2012/0323511 A1 | 12/2012 | Saigo et al. |
| 2013/0069768 A1 | 3/2013 | Madhyastha et al. |
| 2013/0117595 A1 | 5/2013 | Murawski et al. |
| 2013/0127611 A1 | 5/2013 | Bernstein et al. |
| 2013/0148283 A1 | 6/2013 | Forutanpour et al. |
| 2013/0154652 A1 | 6/2013 | Rice et al. |
| 2013/0161380 A1 | 6/2013 | Joyce et al. |
| 2013/0162402 A1 | 6/2013 | Amann et al. |
| 2013/0162403 A1 | 6/2013 | Striemer et al. |
| 2013/0162404 A1 | 6/2013 | Striemer et al. |
| 2013/0164567 A1 | 6/2013 | Olsson et al. |
| 2013/0171479 A1 | 7/2013 | Kim et al. |
| 2013/0183568 A1 | 7/2013 | Babinec et al. |
| 2013/0185008 A1 | 7/2013 | Itabashi et al. |
| 2013/0271072 A1 | 10/2013 | Lee et al. |
| 2013/0295421 A1 | 11/2013 | Teramoto et al. |
| 2013/0320989 A1 | 12/2013 | Inoue et al. |
| 2014/0062663 A1 | 3/2014 | Bourilkov et al. |
| 2014/0139380 A1 | 5/2014 | Ouyang et al. |
| 2014/0176141 A1 | 6/2014 | Takatsuji |
| 2014/0188413 A1 | 7/2014 | Bourilkov et al. |
| 2014/0197802 A1 | 7/2014 | Yamazaki |
| 2014/0225620 A1* | 8/2014 | Campbell ............... B60L 58/12 |
| | | 324/426 |
| 2014/0229129 A1 | 8/2014 | Campbell et al. |
| 2014/0302348 A1 | 10/2014 | Specht et al. |
| 2014/0302351 A1 | 10/2014 | Specht et al. |
| 2014/0320144 A1 | 10/2014 | Nakaya |
| 2014/0342193 A1 | 11/2014 | Mull et al. |
| 2014/0346873 A1 | 11/2014 | Colangelo et al. |
| 2014/0347249 A1 | 11/2014 | Bourilkov et al. |
| 2014/0370344 A1* | 12/2014 | Lovelace ............. H02J 7/0069 |
| | | 429/185 |
| 2014/0379285 A1 | 12/2014 | Dempsey et al. |
| 2015/0061603 A1 | 3/2015 | Loftus et al. |
| 2015/0064524 A1 | 3/2015 | Noh et al. |
| 2015/0072181 A1 | 3/2015 | Roohparvar |
| 2015/0162649 A1 | 6/2015 | Bae et al. |
| 2015/0194839 A1* | 7/2015 | Wojcik .................... H02J 50/80 |
| | | 320/108 |
| 2015/0349391 A1 | 12/2015 | Chappelle et al. |
| 2015/0357685 A1 | 12/2015 | Iwasawa et al. |
| 2016/0034733 A1 | 2/2016 | Bourilkov et al. |
| 2016/0049695 A1 | 2/2016 | Lim et al. |
| 2016/0064781 A1 | 3/2016 | Specht et al. |
| 2016/0092847 A1 | 3/2016 | Buchbinder |
| 2016/0137088 A1 | 5/2016 | Lim et al. |
| 2016/0154025 A1 | 6/2016 | Song et al. |
| 2016/0277879 A1 | 9/2016 | Daoura et al. |
| 2017/0040698 A1 | 2/2017 | Bourilkov et al. |
| 2017/0062841 A1 | 3/2017 | Riemer et al. |
| 2017/0062880 A1 | 3/2017 | Riemer et al. |
| 2017/0092994 A1 | 3/2017 | Canfield et al. |
| 2017/0125855 A1 | 5/2017 | Gong et al. |
| 2017/0176539 A1 | 6/2017 | Younger |
| 2017/0286918 A1 | 10/2017 | Westermann et al. |
| 2017/0301961 A1 | 10/2017 | Kim et al. |
| 2017/0315183 A1 | 11/2017 | Chao et al. |
| 2017/0331162 A1 | 11/2017 | Clarke et al. |
| 2018/0040929 A1 | 2/2018 | Chappelle et al. |
| 2018/0088182 A1 | 3/2018 | Bourilkov et al. |
| 2018/0120386 A1 | 5/2018 | Riemer et al. |
| 2018/0123174 A1 | 5/2018 | Riemer et al. |
| 2018/0123175 A1 | 5/2018 | Riemer et al. |
| 2018/0123176 A1 | 5/2018 | Riemer et al. |
| 2018/0123233 A1 | 5/2018 | Bourilkov et al. |
| 2018/0159225 A1 | 6/2018 | Bourilkov et al. |
| 2019/0113579 A1 | 4/2019 | Riemer et al. |
| 2019/0137572 A1 | 5/2019 | Bourilkov et al. |
| 2019/0194839 A1 | 6/2019 | Ghosh et al. |
| 2020/0011997 A1 | 1/2020 | Dempsey et al. |

FOREIGN PATENT DOCUMENTS

| | | |
|---|---|---|
| CN | 1228540 A | 9/1999 |
| CN | 1315072 A | 9/2001 |
| CN | 1529182 A | 9/2004 |
| CN | 2828963 Y | 10/2006 |
| CN | 101126795 A | 2/2008 |
| CN | 201142022 Y | 10/2008 |
| CN | 201227812 Y | 4/2009 |
| CN | 201233435 Y | 5/2009 |
| CN | 101552363 A | 10/2009 |
| CN | 101702792 A | 5/2010 |
| CN | 101785164 A | 7/2010 |
| CN | 102097844 A | 6/2011 |
| CN | 102142186 A | 8/2011 |
| CN | 102544709 A | 7/2012 |
| CN | 202308203 U | 7/2012 |
| CN | 202720320 U | 2/2013 |
| CN | 202856390 U | 4/2013 |
| CN | 103682482 A | 3/2014 |
| CN | 104427037 A | 3/2015 |
| CN | 104635169 A | 5/2015 |
| CN | 204538140 U | 8/2015 |
| CN | 104953153 A | 9/2015 |
| CN | 105337367 A | 2/2016 |
| CN | 205160145 U | 4/2016 |
| CN | 106405241 A | 2/2017 |
| CN | 106848448 A | 6/2017 |
| CN | 107284272 A | 10/2017 |
| CN | 206804833 U | 12/2017 |
| DE | 10118027 A1 | 11/2002 |
| DE | 10118051 A1 | 11/2002 |
| EP | 0523901 A1 | 1/1993 |
| EP | 1450174 A1 | 8/2004 |
| EP | 1693807 A1 | 8/2006 |
| EP | 1786057 A2 | 5/2007 |
| EP | 1821363 A1 | 8/2007 |
| EP | 2065962 A1 | 6/2009 |
| EP | 2204873 A1 | 7/2010 |
| EP | 2324535 A1 | 5/2011 |
| EP | 2328223 A1 | 6/2011 |
| EP | 2645447 A1 | 10/2013 |
| EP | 2680093 A2 | 1/2014 |
| EP | 2790262 A1 | 10/2014 |
| EP | 3128599 A1 | 2/2017 |
| JP | S52005581 A | 1/1977 |
| JP | 61169781 | 7/1986 |
| JP | 02142324 | 5/1990 |
| JP | H03131771 A | 6/1991 |
| JP | H06284170 A | 10/1994 |
| JP | H06511106 A | 12/1994 |
| JP | H07113855 A | 5/1995 |
| JP | H09005366 A | 1/1997 |
| JP | H0945298 A | 2/1997 |
| JP | 10014003 | 1/1998 |
| JP | 2000067836 A | 3/2000 |
| JP | 2000077928 A | 3/2000 |
| JP | 2001022905 A | 1/2001 |
| JP | 200193510 A | 4/2001 |
| JP | 2003-264009 A | 9/2003 |
| JP | 2004-077480 A | 3/2004 |
| JP | 2004085580 A | 3/2004 |
| JP | 2004-253858 A | 9/2004 |
| JP | 2004-265722 A | 9/2004 |
| JP | 2004534430 A | 11/2004 |
| JP | 2005218174 | 8/2005 |
| JP | 2005327099 A | 11/2005 |
| JP | 2006139544 A | 6/2006 |
| JP | 2006284431 A | 10/2006 |
| JP | 2006324074 A | 11/2006 |
| JP | 2007515848 A | 6/2007 |
| JP | 2007171045 A | 7/2007 |
| JP | 2007-214068 A | 8/2007 |
| JP | 2008042985 A | 2/2008 |
| JP | 2008-530682 A | 8/2008 |

(56)                    References Cited

FOREIGN PATENT DOCUMENTS

| JP | 2008181855 | A  | 8/2008  |
|----|------------|----|---------|
| JP | 2009-37374 |    | 2/2009  |
| JP | 2010098361 | A  | 4/2010  |
| JP | 2010-154012| A  | 7/2010  |
| JP | 2011113759 | A  | 6/2011  |
| JP | 2011203595 | A  | 10/2011 |
| JP | 2012/0056002| A | 3/2012  |
| JP | 2012085491 | A  | 4/2012  |
| JP | 2012-129183| A  | 7/2012  |
| JP | 2012-146447| A  | 8/2012  |
| JP | 2012161614 | A  | 8/2012  |
| JP | 2012-174376| A  | 9/2012  |
| JP | 2012170262 | A  | 9/2012  |
| JP | 2013-038967| A  | 2/2013  |
| JP | 2013038961 | A  | 2/2013  |
| JP | 2013120640 | A  | 6/2013  |
| JP | 2014-203584| A  | 10/2014 |
| KR | 890000323  | A  | 3/1989  |
| KR | 100928563  | B1 | 11/2009 |
| KR | 2011-0018488| A | 2/2011  |
| TW | M510009    | U  | 10/2015 |
| TW | 1580153    | B  | 4/2017  |
| WO | WO-95/01062 | A1 | 1/1995 |
| WO | WO-03/047064 | A2 | 6/2003 |
| WO | WO-2004/047215 | A1 | 6/2004 |
| WO | WO-2004/107251 | A2 | 12/2004 |
| WO | WO-2005/078673 | A1 | 8/2005 |
| WO | WO-2006/048838 | A1 | 5/2006 |
| WO | WO-2006/085291 | A2 | 8/2006 |
| WO | WO-2008/151181 | A1 | 12/2008 |
| WO | WO-2008/156735 | A1 | 12/2008 |
| WO | WO-2009/107597 | A1 | 9/2009 |
| WO | WO-2010/127509 | A1 | 11/2010 |
| WO | WO-2011/063679 | A1 | 6/2011 |
| WO | WO-2011/096863 | A1 | 8/2011 |
| WO | WO-2012/051272 | A2 | 4/2012 |
| WO | WO-2012/061262 | A1 | 5/2012 |
| WO | WO-2012/070635 | A1 | 5/2012 |
| WO | WO-2012/083759 | A1 | 6/2012 |
| WO | WO-2013/022857 | A2 | 2/2013 |
| WO | WO-2013/024341 | A1 | 2/2013 |
| WO | WO-2013/069423 | A1 | 5/2013 |
| WO | WO-2013/084481 | A1 | 6/2013 |
| WO | WO-2013/101652 | A1 | 7/2013 |
| WO | WO-2015/066626 | A1 | 5/2015 |
| WO | WO-2015/183609 | A1 | 12/2015 |
| WO | WO-2016/146006 | A1 | 9/2016 |
| WO | WO-2016/166735 | A1 | 10/2016 |
| WO | WO-2016/172542 | A1 | 10/2016 |

OTHER PUBLICATIONS

International Application No. PCT/US2017/059465, International Search Report and Written Opinion, dated Jan. 18, 2018.

International Application No. PCT/US2017/059466, International Search Report and Written Opinion, mailed May 28, 2018.
International Application No. PCT/US2017/059466, Invitation to Pay Additional Fees And, Where Applicable, Protest Fee, mailed Mar. 22, 2018.
International Application No. PCT/US2017/059466. Written Opinion of the International Preliminary Examining Authority, dated Nov. 22, 2018.
International Application No. PCT/US2017/059469, International Search Report and Written Opinion, Jan. 18, 2018.
International Application No. PCT/US2017/059474, International Search Report and Written Opinion, dated Jan. 19, 2018.
International Preliminary Report on Patentability (IPRP) for International Appl. No. PCT/US2017/059466, dated Feb. 22, 2019.
International Search Report and Written Opinion for corresponding International Application No. PCT/US2017/059472, mailed Jan. 16, 2018.
U.S. Appl. No. 15/842,245, "Battery Including an On-Cell Indicator", filed Sep. 1, 2015.
Yamashiro, Voltage Detecting Circuit, Japanese Patent No. 52005581, Hitashi Ltd., (Jan. 17, 1977), Translated by the United States Patent and Trademark Office via Phoenix Translations (Elgin, TX) in Feb. 2018.
Japanese Patent Application No. 2019-522224, Notice of Reason for Rejection, mailed Jan. 11, 2022.
Chinese Patent Application No. 201780067944.2, First Office Action, mailed Jan. 12, 2022.
Japanese Patent Application No. 2019-522224, Notice of Reason for Rejection, mailed Sep. 10, 2021.
Kooser, Tethercell magically turns AA batteries into Bluetooth devices, CNET.com, downloaded from the Internet at: <https://www.cnet.com/news/tethercell-magically-turns-aa-batteries-into-bluetooth-devices/> (Jan. 8, 2013).
Tethercell Smart Battery Adapter fundraising campaign on Indiegogo website (<https://www.indiegogo.com/projects/tethercell-smart-battery-adapter#/>) (launched Oct. 2013).
Tethercell video uploaded at <https://vimeo.com/53823785> (Oct. 2012).
U.S. Appl. No. 14/842,266, "Battery Including an On-Cell Indicator", filed Sep. 1, 2015.
U.S. Appl. No. 15/340,731, "Single Sided Reusable Battery Indicator", filed Nov. 1, 2016.
U.S. Appl. No. 15/340,737, "Positive Battery Terminal Antenna Ground Plane", filed Nov. 1, 2016.
U.S. Appl. No. 15/340,757, "Dual Sided Reusable Battery Indicator", filed Nov. 1, 2016.
U.S. Appl. No. 15/340,773, "Reusable Battery Indicator with Lock and Key Mechanism", filed Nov. 1, 2016.
U.S. Appl. No. 15/340,789, "Reusable Battery Indicator with Electrical Lock and Key", filed Nov. 1, 2016.

* cited by examiner

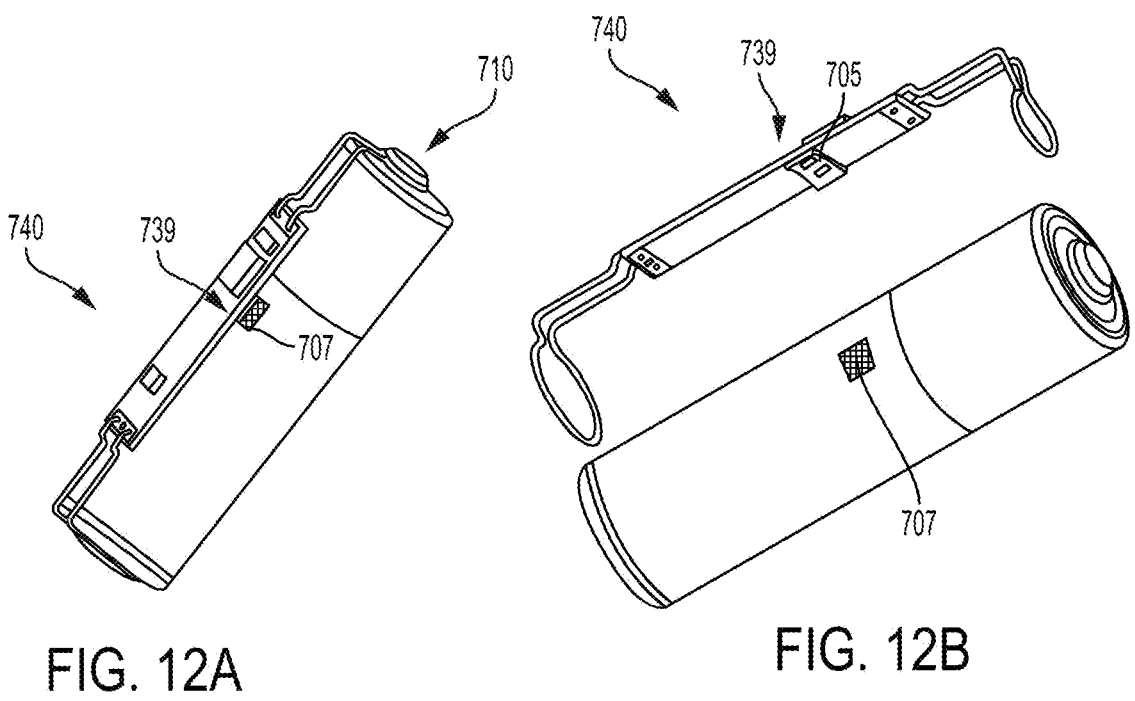
FIG. 12A
FIG. 12B
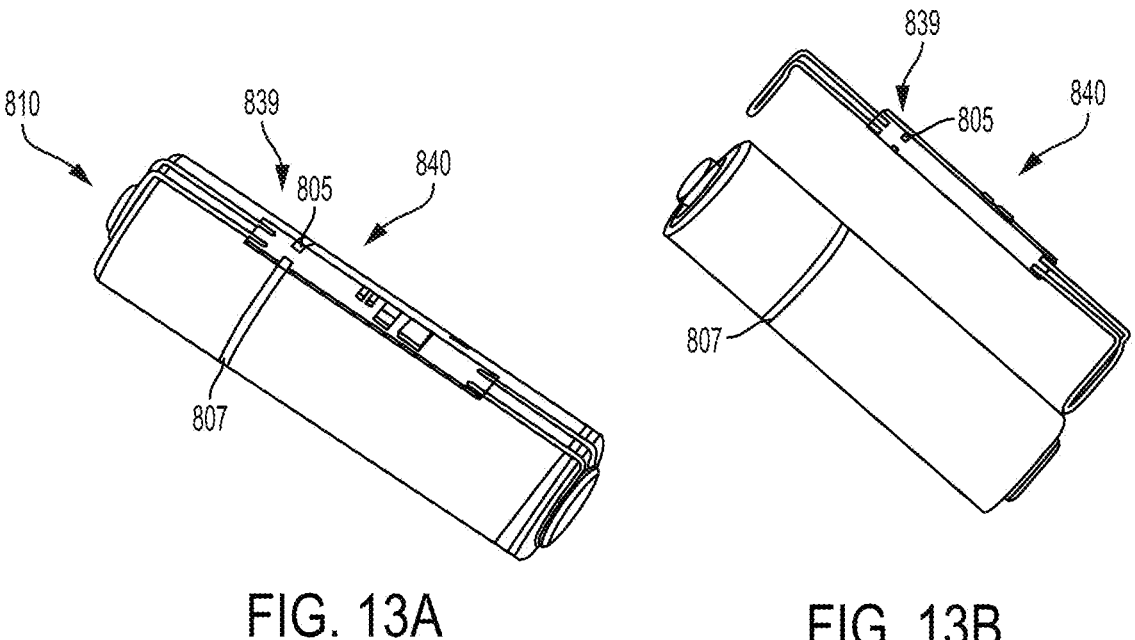
FIG. 13A
FIG. 13B

REUSABLE BATTERY INDICATOR WITH ELECTRICAL LOCK AND KEY

FIELD OF THE INVENTION

The disclosure relates generally to battery indicators and, more specifically, relates to a reusable battery characteristic indicator with an electrical lock and key.

BACKGROUND OF THE INVENTION

Electrochemical cells, or batteries, are commonly used as electrical energy sources. A battery contains a negative electrode, typically called the anode, and a positive electrode, typically called the cathode. The anode contains an electrochemically active anode material that can be oxidized. The cathode contains an electrochemically active cathode material that can be reduced. The electrochemically active anode material is capable of reducing the electrochemically active cathode material. A separator is disposed between the anode and the cathode. The battery components are disposed in a can, or housing, that is typically made from metal.

When a battery is used as an electrical energy source in an electronic device, electrical contact is made to the anode and the cathode, thereby completing a circuit that allows electrons to flow through the device, and which results in respective oxidation and reduction reactions that produce electrical power to the electronic device. An electrolyte is in contact with the anode, the cathode, and the separator. The electrolyte contains ions that flow through the separator between the anode and cathode to maintain charge balance throughout the battery during discharge.

There is a growing need for portable power for electronic devices such as toys; remote controls; audio devices; flashlights; digital cameras and peripheral photography equipment; electronic games; toothbrushes; radios; clocks, and other portable electronic devices. Consumers need to have power readily available for these electronic devices. Because batteries necessarily become depleted of power over time as they are used, consumers need to have access to spare batteries (and/or access to fully recharged rechargeable batteries). It is helpful for a consumer to know the power state of a battery currently in use so that the consumer can have quick access to the needed number of replacement batteries. Batteries come in common sizes, such as the AA, AAA, AAAA, C, and D battery sizes, that have fixed external dimensions and constrained internal volumes per ANSI standard.

Currently, some batteries include on-cell battery charge indicators to help a consumer determine when a battery is nearly depleted and in need of replacement. However, these current on-cell battery charge indicators are single use (i.e., attached to a single battery cell) and cumbersome (because typically two contact buttons must be simultaneously depressed to activate the indicator). Additionally, these on-cell battery indicators require removal of the battery from an electronic device (or package) in order to use the indicator.

SUMMARY OF THE INVENTION

According to one aspect, a battery indicator includes a battery indicator comprises a voltage sensor, a communication circuit, and a connector. The voltage sensor is configured to convert sensed characteristics of a battery to digital information. The communication circuit is communicatively connected to the voltage sensor. The connector is electrically connected to the voltage sensor. The connector is adapted to be removably and electrically connected to the battery, thereby providing an electrical connection between the voltage sensor and the battery. The connector comprises an electronic key component that cooperates with the electronic lock component to enable functionality of the communication circuit.

In accordance with the teachings of the disclosure, the foregoing aspect of a battery indication system may further include any one or more of the following optional forms.

In some optional forms, the battery indicator system further comprises a voltage booster electrically connected to the voltage sensor.

In other optional forms, the electronic lock component comprises a resistor.

In other optional forms, the electronic lock component comprises a capacitor.

In other optional forms, the electronic lock component comprises one of a printed magnetic strip or a magnet.

In other optional forms, the electronic key component comprises a Hall-effect sensor.

In other optional forms, the electronic lock component comprises an optical pattern.

In other optional forms, the electronic key component comprises an optical sensor.

In other optional forms, the optical pattern reflects one of UV or IR wavelength light.

In other optional forms, the electronic lock component comprises a conductive strip.

In other optional forms, the battery indicator system further comprises a computing device communicatively connected to the communication circuit.

In other optional forms, the computing device comprises a processor and a memory, the memory comprising processor executable instructions that, when executed by the processor, cause the processor to determine one of a battery type, a physical location of the battery, or an electrical device that the battery is powering, but communicating with the communications circuit.

BRIEF DESCRIPTION OF THE DRAWINGS

While the specification concludes with claims particularly pointing out and distinctly claiming the subject matter, which is regarded as forming the present invention, the invention will be better understood from the following description taken in conjunction with the accompanying drawings.

FIGS. 12A and 12B are top and bottom perspective views of a seventh embodiment of a reusable battery indicator and a battery cell.

FIGS. 13A and 13B are top and bottom perspective views of an eighth embodiment of a reusable battery indicator and a battery cell.

DETAILED DESCRIPTION OF THE INVENTION

Electrochemical cells, or batteries, may be primary or secondary. Primary batteries are meant to be discharged, e.g., to exhaustion, only once and then discarded. Primary batteries (or disposable batteries) are described, for example, in David Linden, *Handbook of Batteries* (4th ed. 2011). Secondary batteries (or rechargeable batteries) are intended to be recharged and used over and over again. Secondary batteries may be discharged and recharged many times, e.g., more than fifty times, a hundred times, or more. Secondary batteries are described, for example, in David Linden, *Handbook of Batteries* (4th ed. 2011). Accordingly, batteries may include various electrochemical couples and electrolyte combinations. Although the description and examples provided herein are generally directed towards primary alkaline electrochemical cells, or batteries, it should be appreciated that the invention applies to both primary and secondary batteries of aqueous, nonaqueous, ionic liquid, and solid state systems. Primary and secondary batteries of the aforementioned systems are thus within the scope of this application and the invention is not limited to any particular embodiment.

Figure 1:
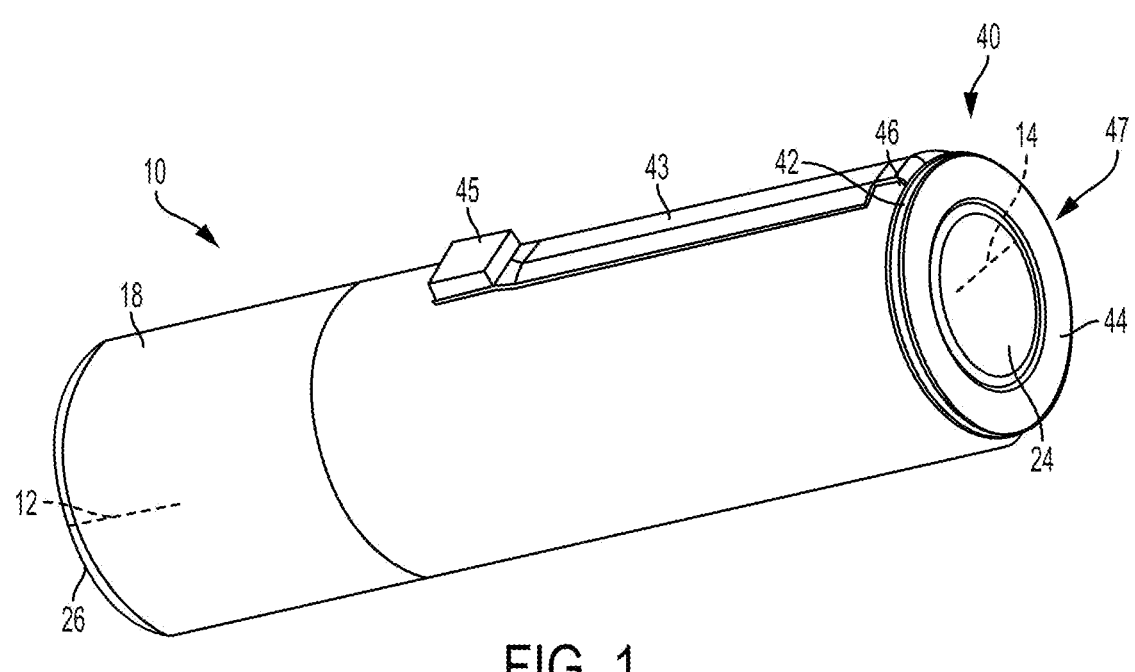
FIG. 1 is a perspective view of a reusable battery indicator constructed in accordance with the teachings of the disclosure, the reusable battery indicator being connected to a battery cell.

Referring to FIG. 1 a primary alkaline electrochemical cell, or battery cell 10, is illustrated that includes a cathode 12, an anode 14, and a housing 18. The battery cell 10 also includes an end cap 24. The end cap 24 serves as a negative terminal of the battery cell 10. A positive pip 26 is located at the opposite end of the battery cell 10 from the end cap 24. The positive pip 26 serves as a positive terminal of the battery cell 10. An electrolytic solution is dispersed throughout the battery cell 10. The battery cell 10 can be, for example, a AA, AAA, AAAA, C, or D alkaline battery. Additionally, in other embodiments, the battery cell 10 can be a 9V battery, a camera battery, a watch battery, or any other type of primary or secondary battery.

The housing 18 can be made of any suitable type of housing base material, for example cold-rolled steel or nickel-plated cold-rolled steel. In the embodiment illustrated in FIG. 1, the housing 18 may have a cylindrical shape. In other embodiments, the housing 18 may have any other suitable, non-cylindrical shape. The housing 18, for example, may have a shape comprising at least two parallel plates, such as a rectangular, square, or prismatic shape. The housing 18 may be, for example, deep-drawn from a sheet of the base material, such as cold-rolled steel or nickel-plated steel. The housing 18 may be, for example, drawn into a cylindrical shape. The housing 18 may have a sidewall. The interior surface of the sidewall of the housing 18 may be treated with a material that provides a low electrical-contact resistance between the interior surface of the sidewall of the housing 18 and an electrode, such as the cathode 12. The interior surface of the sidewall of the housing 18 may be plated, e.g., with nickel, cobalt, and/or painted with a carbon-loaded paint to decrease contact resistance between, for example, the internal surface of the sidewall of the housing 18 and the cathode 12.

Attached to the battery cell 10 is one embodiment of communication mechanism, such as a reusable battery indicator 40. The reusable battery indicator 40 attaches to one end of the housing 18, in the embodiment illustrated in FIG. 1, to the negative or end cap 24 end of the housing 18. The reusable battery indicator 40 includes an integrated circuit, which may be incorporated into a printed circuit board (PCB) 42 (in one embodiment, the PCB is a multi-layered insulator/conductive structure that can be a rigid epoxy, FR4 phelonic with bonded copper traces, or a flexible polyester, polyamide with bonded copper traces), which is sandwiched between a first connector 44 that is electrically connected to the PCB 42, and a retainer 46 that is electrically connected to the PCB 42. The first connector 44 and the retainer 46 form part of an electrical lock and key mechanism 39, which will be further described below.

The PCB 42 may have a generally annular shape, as illustrated in FIG. 1, and the PCB 42 may extend into a flexible PCB 43, which extends along an outer surface of the housing 18, generally away from the first connector 44 and from the retainer 46. At one end of the flexible PCB 43, additional electrical components may be located, such as a chip antenna 45, an IC, an IC with integral antenna, or passive components. Placing some electrical components, such as the antenna 45, at one end of the flexible PCB 43 may provide a more advantageous location for certain electrical components. For example, locating the antenna 45 at one end of the flexible PCB 43 may provide better transmission characteristics than locating the antenna closer to the first connector 44 and to the retainer 46. The antenna 45 may also be formed as an integral part of the flexible PCB 43 or of the rigid PCB 42 as part of the copper trace layer.

The first connector 44 may be removably and electrically connected to the end cap 24 to form a negative electrical connection and the retainer 46 may be removably and electrically connected to the housing 18, which generally has a positive electrical charge, to form a positive electrical connection. The first connector 44 and the retainer 46 may take virtually any physical form that allows the first connector 44 and the retainer 46 to form electrical connections with the battery cell 10 and the PCB 42 and that does not impede normal device terminal access. The first connector 44 and the retainer 46 may be formed from virtually any material that transmits analog information, such as electrical information, from the battery cell to the PCB 42. For example, in some embodiments, the first connector 44 and retainer 46 may be formed from one or more of the following materials, a metal, a metal alloy, cold-rolled steel, hard drawn ferrous and non-ferrous alloys, high and low carbon steel alloys, post or pre-plated ferrous and non-ferrous alloys, or any combination thereof. In some embodiments, at least one of the first connector 44 and the retainer 46 may comprise a metal and an insulator. In some embodiments, an insulator may be a non-conductive coating (such as a polymer layer, epoxy, or passivate) that is applied to the connector/retainer or an additional insulator ring (such as paper, phenolic, or polymer).

Generally, the integrated circuit receives electrical information, such as amperes or volts from the first connector 44 and from the retainer 46, and the electrical information is used by the integrated circuit to calculate battery characteristic information, such as power or charge level, and the integrated circuit then transmits the battery characteristic information to a receiver, such as a computer, a smart phone, or a personal digital assistant, for use by the consumer. In this way, the reusable battery indicator 40 allows a consumer to acquire the battery characteristic information without removing the battery cell from an electronic device (or from a package). The first connector 44 and the retainer 46 deliver the electrical information to the integrated circuit without interfering with electrical contacts between the battery cell and the electronic device. Furthermore, the reusable battery indicator 40 is movable from one battery cell to another battery cell so as to be reused over and over again, thereby reducing the overall cost to a consumer.

Figure 2:
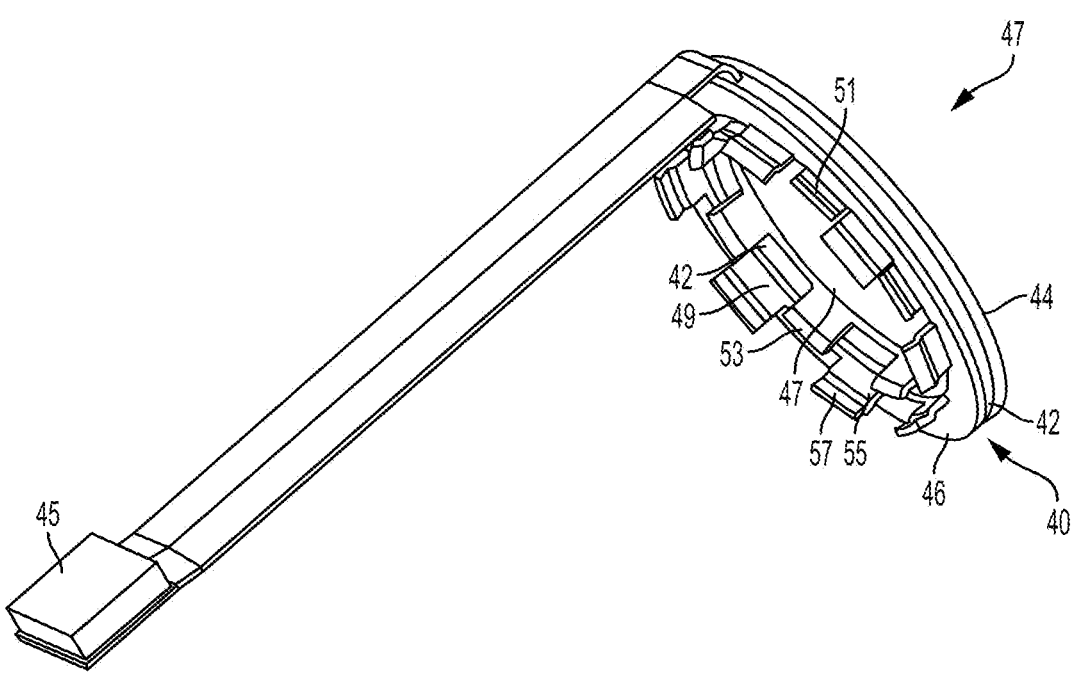
FIG. 2 is a bottom perspective view of the reusable battery indicator of FIG. 1.

Referring to FIG. 2, the reusable battery indicator 40 is illustrated in more detail. The first connector 44 is annularly shaped and located on an opposite side of the PCB 42 from the retainer 46, which is also annularly shaped. The first connector 44 includes a central opening 47, which is sized and shaped to surround a raised central portion of the end cap 24. Similarly, the retainer 46 includes a central opening 49 that is sized and shaped to surround the raised central portion of the end cap 24. Thus, the first connector 44, the PCB 42, and the retainer 46 form a ring-shaped (or annularly-shaped) sandwich structure that is sized to fit on one end (the negative end) of the battery cell 10.

The first connector 44 includes a plurality of connector tabs 51. The connector tabs 51 extend away from the first connector 44 and towards the retainer 46. The connector tabs 51 are spaced radially inward (towards a center of the central opening 47) from the retainer 46. More specifically, the connector tabs 51 are separated from the retainer 46 by the PCB 42. The connector tabs 51 are arranged to contact the end cap 24 of the battery cell 10, as will be further explained below. Additionally, the connector tabs 51 include crimped ends 53, which facilitate a removable connection with the end cap 24.

The retainer 46 includes a plurality of retainer tabs 55. The retainer tabs 55 extend away from the first connector 44. The retainer tabs 55 are spaced radially outward (away from a center of the central opening 59). More specifically, the retainer tabs 55 are separated from the first connector 44 by the PCB 42. The retainer tabs 55 are arranged to contact the can or housing 18 of the battery cell 10, as will be further explained below. Additionally, the retainer tabs 51 include crimped ends 57, which facilitate a removable connection with the housing 18.

Figure 3:
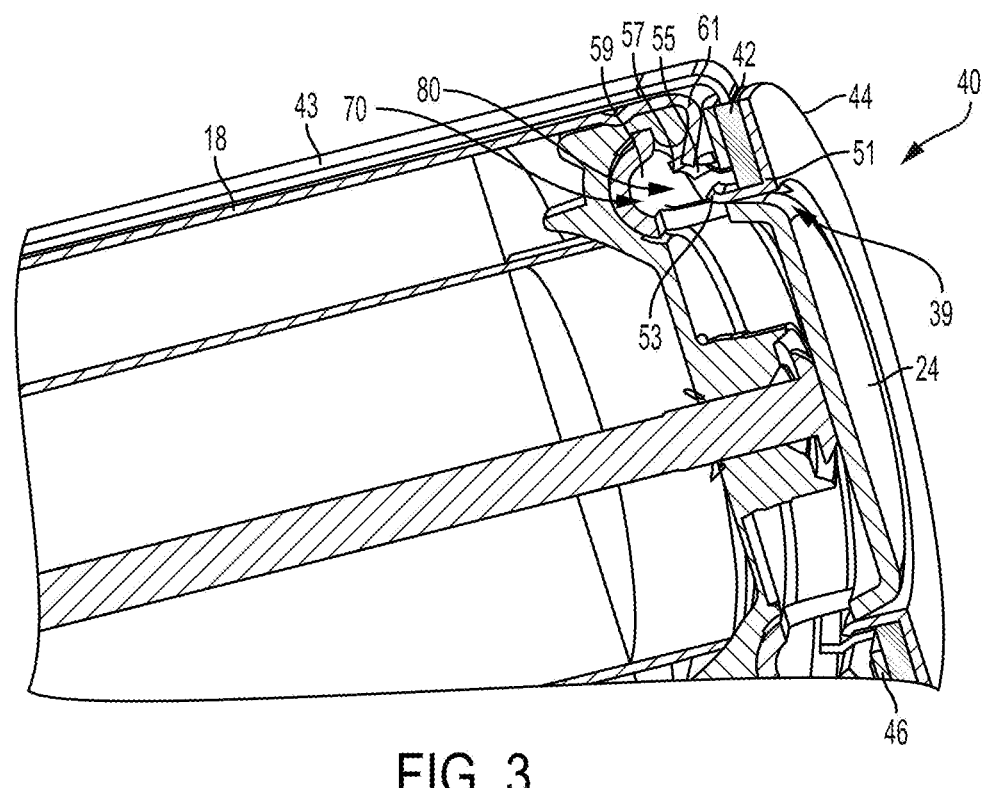
FIG. 3 is side cross-sectional view of the reusable battery indicator and battery cell of FIG. 1.

Referring now to FIG. 3, the PCB 42 is radially thicker than the retainer 46. As a result, the retainer tabs 55 are located radially outward of the connector tabs 51. The retainer tabs 55 extend into a can void 59 that is formed between a crimped wall 61 of the housing 18 and the end cap 24. As the battery indicator 40 is pressed onto the end cap 24, the crimped ends 57 of the retainer tabs 55 are pushed radially inward until the crimped ends 57 pass over an end of the crimped wall 61 of the housing 18, at which point, the crimped ends 57 expand radially outward to removably lock the retainer 46 in place on the end of the housing 18 and to provide a positive electrical connection (because the housing carries a positive charge).

Similarly, the connector tabs 51 extend into the can void 59, but the connector tabs 51 are located against the end cap 24. As the battery indicator 40 is pressed onto the end cap, the connector tabs 51 are pushed radially outward, which maintains physical contact between the connector tabs 51 and the end cap to provide a negative electrical connection (because the end cap carries a negative charge). As a result, the PCB 42 receives electrical information (e.g., volts and amperes) through the connector tabs 51 and through the retainer tabs 55.

The electrical lock and key mechanism 39 comprises the first connector 44, the retainer 46, the crimped wall 61, the end cap 24, and the can void 59. Essentially, the can void 59, which is formed by the space between the crimped wall 61 and the end cap 24, forms an electrical lock assembly 70. The can void 59 is arranged so that connection to the positive terminal of the battery cell 10 is available on one side (the radially outward side in FIG. 3) and connection to the negative terminal of the battery cell 10 is available on the other side (the radially inward side in FIG. 3). In other embodiments, the positive and negative connections may be reversed.

An electrical key 80 comprises the connector tabs 51 and the retainer tabs 55 and the PCB 42 may be electrically connected in series between the connector tabs 51 and the retainer tabs 55. Electrical connections can only be established if the electrical key 80 is formed to correctly contact the electrical lock 70 when the battery indicator 40 is connected to one end of the battery cell 10. Without the radial spacing of the connector tabs 51 and the retainer tabs 55, the battery indicator 40 would not establish the correct electrical connections and the battery indicator 40 would not receive power, and/or the battery indicator 40 would not receive the battery characteristic information that is used by the integrated circuit. For example, the connector tabs 51 and the retainer tabs 55 may not come into contact with one another or create a condition where a substantially low electrical impedance exists between the connector tabs 51 and the retainer tabs 55. Furthermore, any intended rotation or motion of the connector tabs 51 and retainer tabs 55 with respect to one another may not cause such contact or low electrical impedance.

In other embodiments, an electrical lock circuit could be formed in the crimped wall 61 in a manner in which contact by the retainer tabs 55 completes the electrical lock circuit and the integrated circuit would allow the battery characteristic analysis to continue only if the electrical lock circuit was completed. Such an electrical lock circuit would supplement the electrical lock and key mechanism 39 described above.

Figure 4:
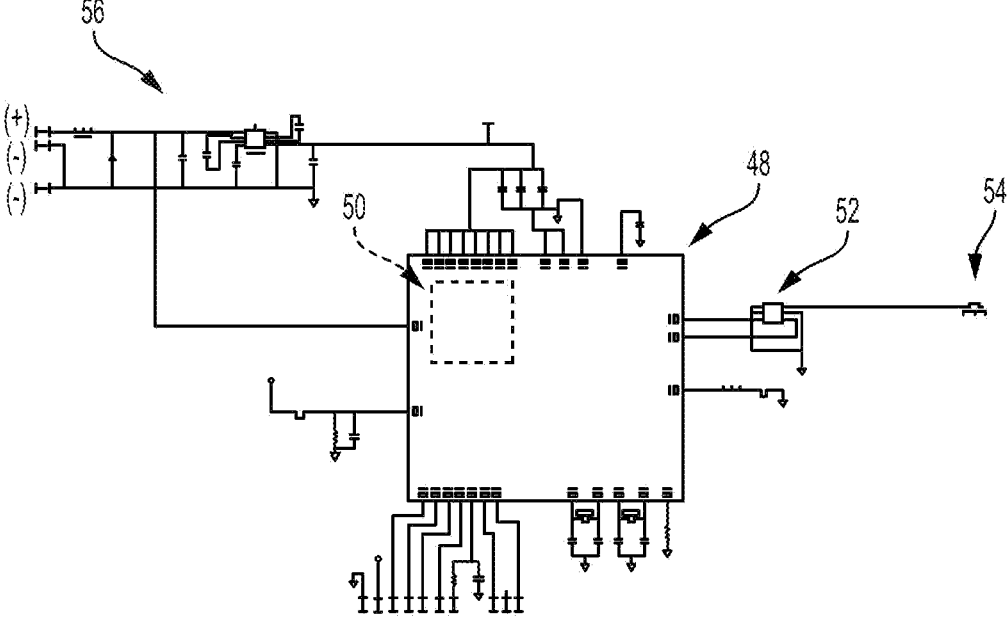
FIG. 4 is an electronic circuit schematic diagram of the reusable battery indicator of FIG. 1.
Figure 5:
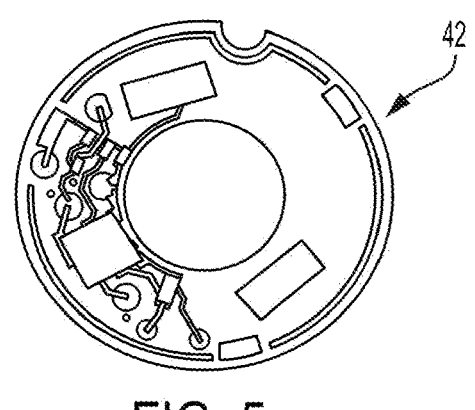
FIG. 5 is a top plan view of a printed circuit board of the reusable battery indicator of FIG. 1.

Turning now to FIGS. 4 and 5, formed on the PCB 42 is an integrated circuit 48, that includes an embedded voltage sensor 50 within the integrated circuit 48 that is communicatively connected to the first connector 44 and to the retainer 46. The embedded voltage sensor 50 senses analog characteristics of the battery cell, such as amperes and voltage, and converts the sensed analog characteristics to digital information. The PCB 42 also includes a communication circuit 52. An antenna 54 is operatively coupled to the communication circuit 52. The communication circuit 52 may comprise one or more of a radio-frequency identification circuit, a Bluetooth® circuit, a Bluetooth® low energy circuit, a Wi-Fi circuit, a Zigbee® circuit, a LORA circuit, and a Z-wave circuit. In one embodiment, an integrated circuit, such as a wireless Bluetooth Low-Energy voltage sensor, may incorporate the analog to digital converter, a microcontroller, a Bluetooth radio, a memory device, and a DC/DC voltage converter.

A voltage booster 56 is electrically connected to the integrated circuit 48 and the embedded voltage sensor 50.

The embedded voltage sensor 50 and the voltage booster 56 are capable of reading the open circuit voltage of the battery that may be, for example, less than 1.8 volts. In some embodiments, the communication circuit 52 may comprise one or more of a thin disc BLE module, a UHF module, or a RF module.

In the embodiment illustrated in FIGS. 4 and 5, the integrated circuit 48, the voltage sensor 50, and the communication circuit 52 are all formed on the PCB 42, which is connected to the first connector 44 and to the retainer 46. However, in other embodiments, the integrated circuit 48, the voltage sensor 50, and the communication circuit 52 may be formed as separate components that are communicatively and operatively connected to one another.

Figure 6:
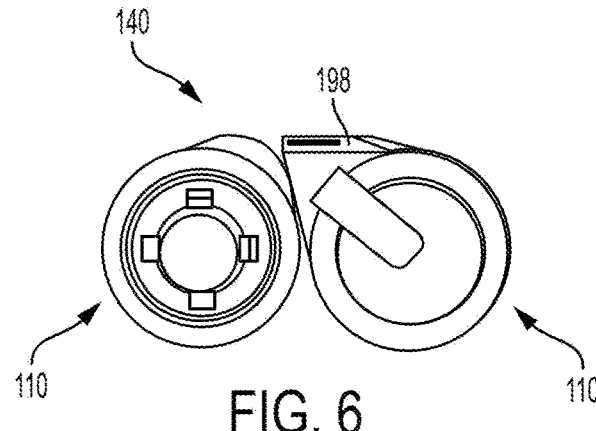
FIG. 6 is an end elevational view of a second embodiment of a reusable battery indicator constructed in accordance with the teachings of the disclosure.

In the embodiment illustrated in FIG. 6, similar elements are numbered exactly 100 greater than elements numbered in FIGS. 1-5. For example, the battery cell is numbered 10 in FIGS. 1-4 and the battery cell is numbered 110 in FIG. 6. Unless stated otherwise, any element from any illustrated embodiment may be incorporated into any other illustrated embodiment.

Turning now to FIG. 6, a second embodiment of the reusable battery indicator 140 is attached to a battery cell 110. The reusable battery indicator 140 is illustrated and located between two battery cells 110. In the embodiment of FIG. 6, the reusable battery indicator 140 includes a housing 198 that has only a single concave side able to fit into and up to the entire triangular prism void area delineated by the one or more batteries and the battery receptacle.

Figure 7:
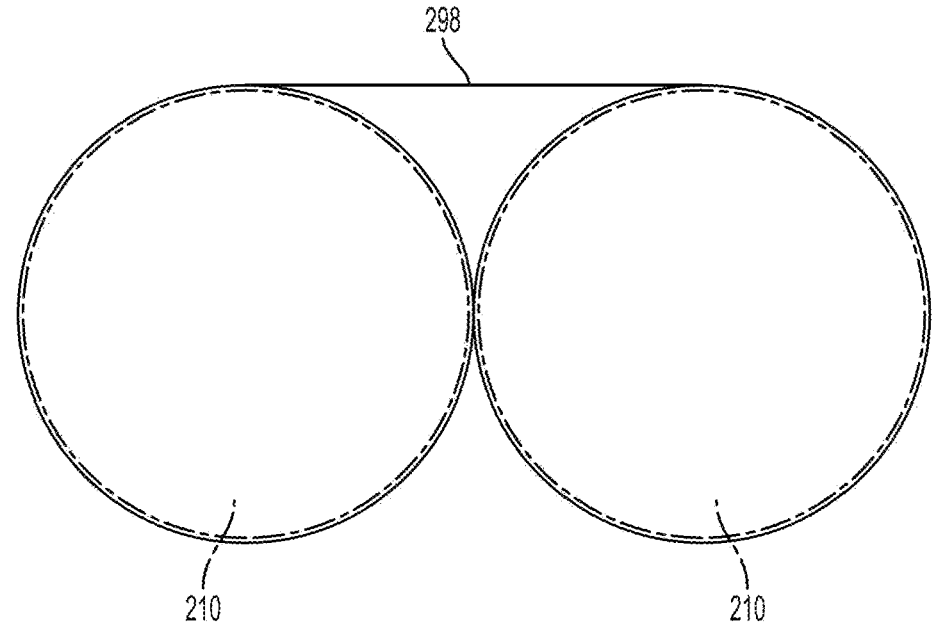
FIG. 7 is an end elevational view of a third embodiment of a reusable battery indicator constructed in accordance with the teachings of the disclosure.

FIG. 7 illustrates an alternative housing shape area for which the reusable battery indicator can fit into. In this embodiment, the housing 298 is arranged to fit in the void formed by two cylindrical battery cells 210 that are arranged side by side and oriented such that the respective longitudinal axes of the battery cells 210 are parallel to one another. In the embodiment illustrated in FIG. 7, the housing 298 has a cross-sectional shape that is defined by the following equation:

$$A_v = (D_B^2 - \Pi/4 \times D_B^2)/2, \text{ where}$$

$A_v$ is the cross-sectional area of the housing 298; and $D_B$ is a diameter of one battery cell 210.

A housing having a cross-sectional shape defined by the preceding equation maximizes the usable space between the battery cells. For example, a housing having the cross-sectional shape defined above would result in the following housing volumes for the given battery sizes (assuming that the housing length was equal to the battery cell length). For a AAA battery, the housing would have a volume of 526 mm³; and for a AA battery, the housing would have a volume of 1140 mm³. In other embodiments, the housing may have a cross-sectional shape that fits within the shape $A_v$, or that fits within a shape equal to $A_v/2$ in the case of a single battery cavity. For example, the housing may have a cross-sectional shape that is one of rectangular, trapezoidal, elliptical, semi-circular, and variable prism that fits within one of the above described voids.

Figure 8:
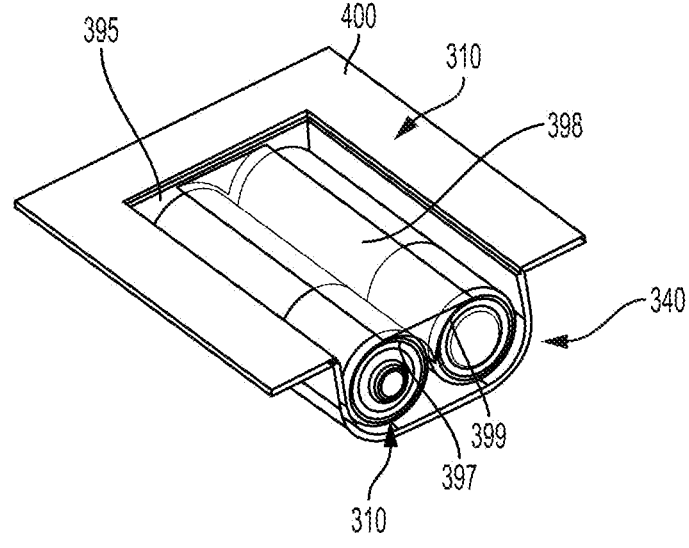
FIG. 8 is a bottom perspective view of a battery compartment of an electronic device including two battery cells and a fourth embodiment of a reusable battery indicator that is connected to one of the battery cells.

Turning now to FIG. 8, yet another alternative embodiment of a reusable battery indicator 340 is illustrated. In the embodiment of FIG. 8, the reusable battery indicator includes a housing 398, the integrated circuit, the voltage sensor, and the communication circuit being mounted within the housing 398. In the embodiment of FIG. 8, the housing 398 is sized and shaped to fit between two cylindrical battery cells 310 that are arranged longitudinally side-by-side. In the embodiment illustrated in FIG. 8, the housing 398 has a cross-section that is in the shape of a triangular prism. More specifically, the housing 398 has a first side 397 that is concave and a second side 399 that is concave. In the embodiment of FIG. 8, the reusable battery indicator 340 is mounted between the battery cells 310 and within a battery receptacle 395 of an electronic device 400.

Figure 9:
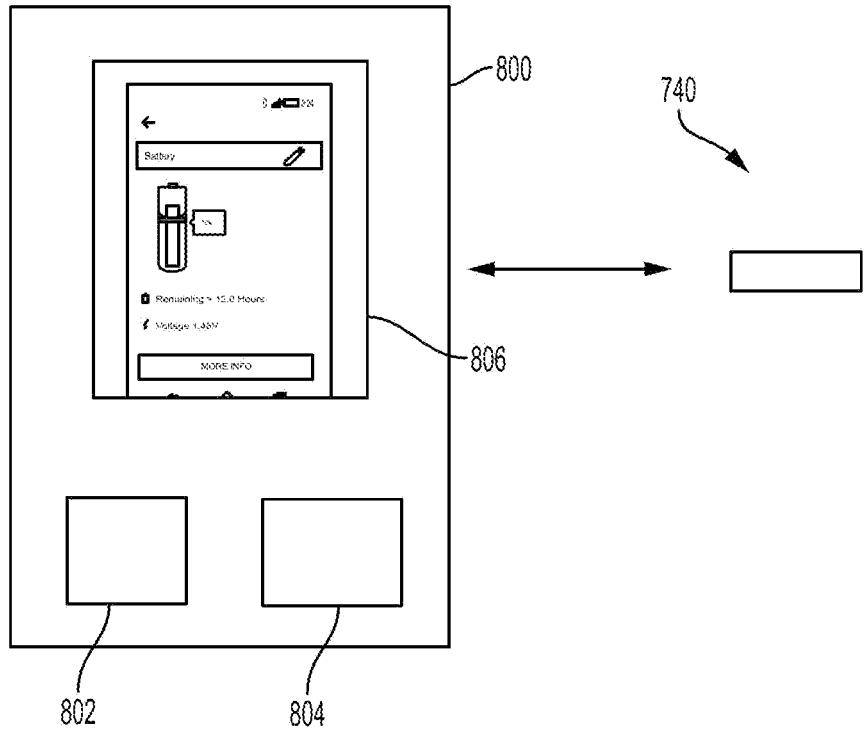
FIG. 9 is a a schematic diagram of a battery indication system including the reusable battery indicator of FIG. 1

Turning now to FIG. 9, a computing device 800 is communicatively connected to the communication circuit in the reusable battery indicator 740. The computing device receives information from the communication circuit through wireless signals sent by the antenna in the reusable battery indicator 740. For example, the wireless signal may be one or more of a wifi signal, a Bluetooth® signal, a RFID signal, or any other wireless signal. In other embodiments, the computing device 800 and the reusable battery indicator 740 may be communicatively connected by a wired connection.

The computing device 800 includes a processor 802 and a memory 804. The memory 804 may store processor executable instructions that, when executed by the processor 802, cause the processor 802 to detect a wireless communication signal from the reusable battery indicator 740. In some embodiments the memory 804 may comprise a non-transitory computer readable medium with the processor executable instructions embedded thereon as an article of manufacture. The processor executable instructions may also cause the processor 802 to send wireless signals back to the reusable battery indicator 740 to remotely control battery circuitry through the reusable battery indicator 740. In this manner, the processor 802 may cause the reusable battery indicator 740 to determine battery characteristic data; and to send the battery characteristic data to a user interface, such as a display 806 on the computing device 800.

In some embodiments, the battery characteristic data may comprise at least one of an electrical capacity; a voltage; an impedance, a temperature, a current; an age, a charge/discharge cycle count, and a coulomb count.

In other embodiments, the processor executable instructions, when executed by the processor 802, causes the processor 802 to determine at least one of a battery type, a physical location of the battery, and an electrical device that the battery is powering by communicating with the reusable battery indicator 740.

Figures 10A, 10B, 11A, 11B:
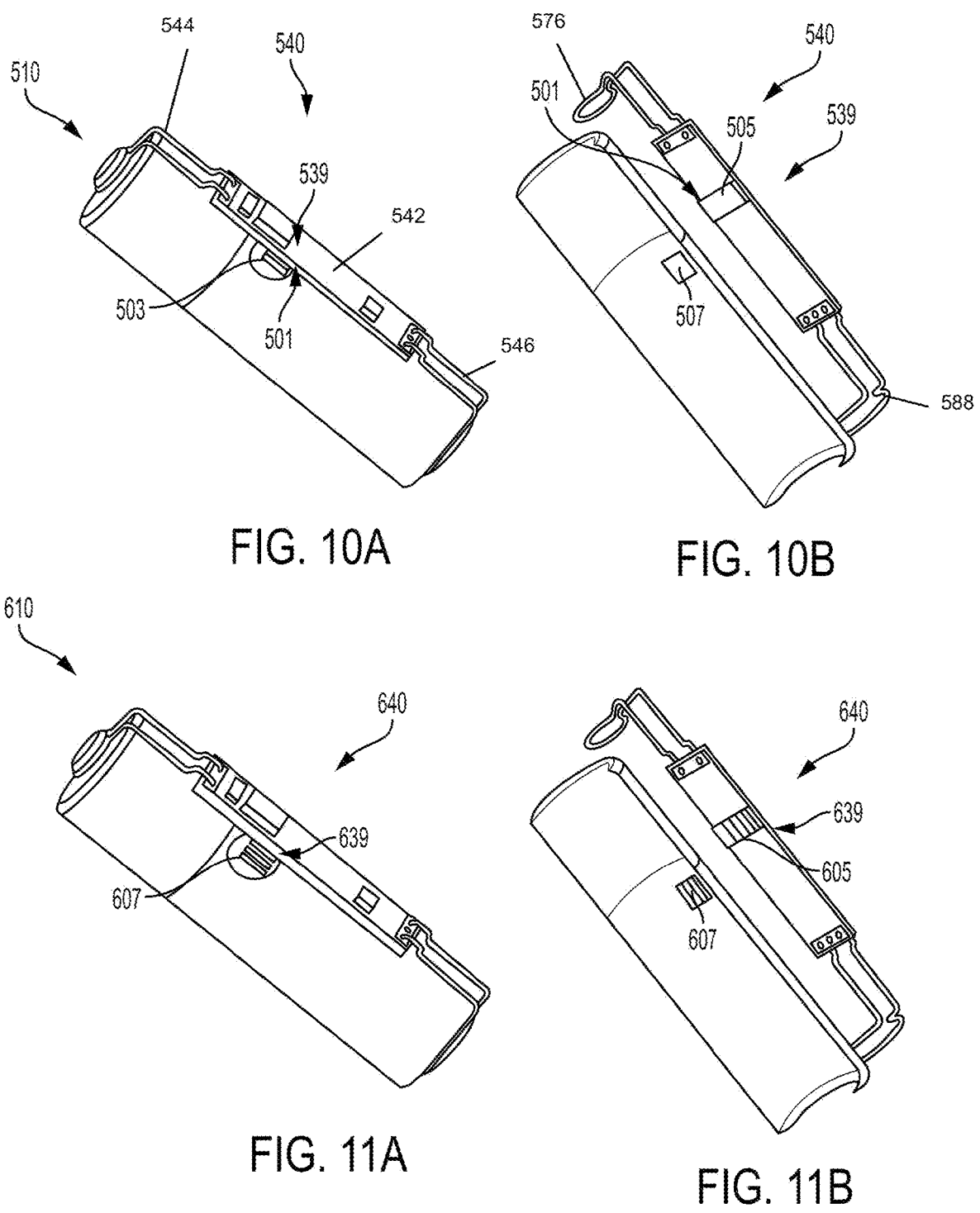
FIGS. 10A and 10B are top and bottom perspective views of a fifth embodiment of a reusable battery indicator and a battery cell.
FIGS. 11A and 11B are top and bottom perspective views of a sixth embodiment of a reusable battery indicator and a battery cell.

Turning now to FIGS. 10A and 10B, yet another embodiment of a reusable battery indicator 540 is illustrated. The reusable battery indicator 540 is attached to a battery cell 510. The reusable battery indicator 540 includes a PCB 542, a first connector 544, and a second connector 546. While the battery cell 510 in FIGS. 10A and 10B is illustrated as a AA size battery, the illustration is not intended to limit the reusable battery indicator 540 to the illustrated battery cell 510. Rather, the reusable battery indicator 540 may be sized and shaped to fit virtually any battery cell, especially those battery cell sizes listed elsewhere in the specification.

In the embodiment illustrated in FIGS. 10A and 10B, the first connector 544 and the second connector 546 comprise flexible wires. The flexible wires may be formed as spring wires (from hard drawn ferrous and non-ferrous spring alloys) that capture the positive battery terminal and the negative battery terminal to transmit electrical characteristics, such as voltage and amperes, to the integrated circuit formed on the PCB 542. In one embodiment, the spring wires may be formed of ASTM A228 music wire with re or post nickel plating to enhance conductivity, to reduce contact resistance, and to provide corrosion resistance.

In the embodiment illustrated in FIGS. 10A and 10B, the flexible wires include a first end, which is connected to a positive terminal on the PCB 542 and a second end, which is also connected to the positive terminal on the PCB 542. Other embodiments may include single ended wires. The flexible wires are oriented substantially parallel to a longitudinal axis of the battery cell 510. The flexible wires form end loops 576, 588, which lie in a plane that is substantially perpendicular to the longitudinal axis of the battery cell 510. The end loop 576 is sized and shaped to fit around the positive terminal of the battery cell 510 and the end loop 588 is sized and shaped to fit around the negative terminal. As a result, the flexible wire forms a positive electrical pathway from the positive battery terminal to the positive terminal on the PCB 542 and from the negative battery terminal to the negative terminal on the PCB 542. Moreover, the flexible wires may be formed to produce a spring force that biases the flexible wires into the attached position illustrated in FIG. 10A, while allowing the flexible wires to be temporarily deformed by a user to remove the reusable battery indicator 540 from the battery cell 510 when desired, as illustrated in FIG. 10B.

In some embodiments, one or more of the flexible wires may include a conductive magnet, or the one or more of the flexible wires may be formed from conductive magnetic material, to provide additional retention force between the first flexible wires and the battery terminals.

In other embodiments, one or more of the flexible wires may be formed as a Kelvin connection, including separate power and sensing terminals, to measure impedance. Additionally, in alternate embodiments, the flexible wires need not be formed as a single continuous wire, but may be formed as multiple wire pieces, for example, two wire pieces that are separated by a small distance in the end loop.

In the embodiment of FIGS. 10A and 10B, an electronic lock and key mechanism 539 includes a split matching antenna network as part of a wireless module antenna 501. A first electronic lock, which is formed as a printed electronic component on the battery label, includes a carbon film resistor or capacitor 503 that tunes or de-tunes the wireless module antenna 501. In other words, the wireless module antenna 501 requires the presence of the capacitor 503 (and thus the battery 510) for completion and tuning of the antenna circuit. A split capacitor may be created using a conductive plate 505 on the underside of the wireless module antenna 501 and a conductive plate 507 on the backside of the battery label film (facing the cell can) with the PVC battery label acting as a dielectric between the two capacitor plates. Split capacitors may also be used as a passive component which is part of the electronic module enable circuitry.

Turning now to FIGS. 11A and 11B, yet another embodiment of a reusable battery indicator 640 is illustrated. In the embodiment of FIGS. 11A and 11B, an electronic lock and key assembly 639 is formed by a Hall-effect sensor and circuit 605 on the electronic module and a printed magnetic strip 607, array, or symbol on the battery 610 label. Installation of the electronic module onto the battery creates a coupled magnetic sensor system. Rotation or translation of the electronic module (relative to the battery) results in a magnetic field pulse generated in the hall-effect sensor. Signal conditioning circuitry on the electronic module generates an enable pulse to the electronic module radio thereby enabling functionality.

Turning now to FIGS. 12A and 12B, yet another embodiment of a reusable battery indicator 740 is illustrated. The reusable battery indicator 740 includes an electronic lock and key assembly 739. The electronic lock and key assembly 739 includes a lock, such as an optical ID reflective pattern 707, text, or, symbol on the battery 710 label and an optical transmitter/sensor 705 on the electronic module. Installation of the electronic module onto the optical ID reflective pattern 707 creates a coupled system. Presence, rotation or translation of the electronic module (relative to the battery) results in a varied optical signal relative to sensing reflective changes of the label pattern. Use of a luminous (e.g., fluorescent) coating on the label may create a response sensor to enable electronic module functionality. In other embodiments, a light generator/sensor on the electronic module may activate the fluorescent coating with a led flash during initial power-up and may sense residual photon activity which activates electronic module operation. Alternately, use of a printed carbon/iron matrix pattern in conjunction with a magnetic field generator to sense eddy currents related to a particular pattern may enable electronic module functionality. Optional use of a reflective opto-isolator at a set reflective angle in conjunction with a curved reflective element on battery surface may also enable electronic module functionality. In some embodiments, a Fresnel lens (flip/flop) or a louvered mask may isolate reflected light (visible, UV, IR) to a particular vector matched to the receiver vector.

Turning now to FIGS. 13A and 13B, yet another embodiment of a reusable battery indicator 840 is illustrated. The reusable battery indicator 840 includes an electronic lock and key assembly 839. The electronic lock and key assembly 839 includes a capacitive coupling connection having a label capacitive connector 807, which may be a foil pad with label micro piercings, and the electronic module has companion foil pad 805 with a deformable conductive polymer. When the foil pad 805 contacts the label capacitive connector 807, electronic functionality is enabled. In the embodiment of FIGS. 13A and 13B, the label capacity connector 807 is in the form of a conductive strip or ring on the product label, which creates an electrical coupling when the electronic module is installed on the battery 810. The conductive label strip may be formed by an adhesive metal that is foil applied to the battery label or is printed directly on the battery label with a conductive ink (e.g., carbon/graphite or metal loaded ink). The conductive label strip provides resistive, capacitive, or inductive characteristics provided by metal alloy characteristics or metal loading of the conductive ink. An electronic module measuring or response circuit may be tuned to the electrical characteristics of the conductive strip to provide communication or function only the authorized strip completes the circuit.

In other yet other embodiments, a reflective aperture may be used to isolate a radio wave to a particular direction and to provide a directional receiver antenna tuned to receive from that particular direction. In yet other embodiments, a user may be required to scan the battery label and to authorize activation of the electronic module with a software application that enables electronic module functionality.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A battery indicator comprising:
a voltage sensor, the voltage sensor being configured to convert sensed characteristics of a battery to digital information;
a communication circuit, the communication circuit being communicatively connected to the voltage sensor;
an antenna operatively coupled to the communication circuit;
a connection mechanism having a first connector and a second connector that are electrically connected to the voltage sensor, the first connector and the second connector being adapted to be removably connected to a first battery terminal and to a second battery terminal, respectively, thereby providing an electrical connection between the voltage sensor and the first and second battery terminals; and
an electrical key component that is configured to read an electrical lock component comprising a printed electronic component or a printed optical component on a battery label, and the electrical key component is also configured to enable functionality of the communication circuit when in the presence of the electrical lock component;
wherein the electrical key component comprises a split antenna matching network, an optical sensor, a capacitive coupling connection, or a Hall-effect sensor.

2. The battery indicator of claim 1, further comprising a voltage booster electrically connected to the voltage sensor.

3. The battery indicator of claim 1, wherein the electronic lock component comprises a resistor printed on the battery label.

4. The battery indicator of claim 1, wherein the electronic lock component comprises a capacitor printed on the battery label.

5. The battery indicator of claim 1, wherein the electronic lock component comprises one of a magnetic strip or a magnet printed on the battery label.

6. The battery indicator of claim 1, wherein the electronic lock component comprises an optical pattern printed on the battery label.

7. The battery indicator of claim 6, wherein the optical pattern reflects one of UV or IR wavelength light.

8. The battery indicator of claim 1, wherein the electronic lock component comprises a conductive strip printed on the battery label.

9. The battery indicator of claim 1, further comprising a computing device communicatively connected to the communication circuit.

10. The battery indicator of claim 9, wherein the computing device comprises a processor and a memory, the memory comprising processor executable instructions that, when executed by the processor, cause the processor to determine one of a battery type, a physical location of the battery, or an electrical device that the battery is powering, but communicating with the communications circuit.

11. The battery indicator of claim 1, wherein the communication circuit comprises at least one of radio-frequency identification circuitry, Bluetooth circuitry, Bluetooth low energy circuitry, Wi-Fi circuitry, Zigbee circuitry, LORA circuitry, and Z-wave circuitry.

12. The battery indicator of claim 1, wherein the voltage sensor is capable of reading an open circuit voltage of less than 1.8 Volts.

13. The battery indicator of claim 1, wherein the split matching antenna network includes a wireless module antenna that requires the presence of the printed component to function.

14. The battery indicator of claim 1, wherein the capacitive coupling connection comprises a foil pad with a deformable conductive polymer.

15. The battery indicator of claim 1, wherein the first connector includes a central opening sized and shaped to surround a raised central portion of an end cap of a battery terminal.

16. The battery indicator of claim 1, wherein the voltage sensor and the communication circuit are formed on a PCB.

17. The battery indicator of claim 1, wherein the first connector or the second connector comprises a flexible wire.

18. The battery indicator of claim 17, wherein the flexible wire comprises a spring wire.

19. The battery indicator of claim 17, wherein the spring wire comprises a spring force that biases the flexible wire into an attached position.

20. The battery indicator of claim 17, wherein the flexible wire comprises an end loop.

* * * * *